(12) United States Patent
Ignatyev et al.

(10) Patent No.: US 7,585,994 B2
(45) Date of Patent: Sep. 8, 2009

(54) PROCESS FOR THE PREPARATION OF COMPOUNDS CONTAINING PERFLUOROALKANESULFONIC ACID GROUPS

(75) Inventors: Nikolai Ignatyev, Duisburg (DE); Michael Schmidt, Seeheim-Jugenheim (DE); Udo Heider, Winchester (GB); Peter Sartori, Utting (DE); Andry Kucheryna, Wuppertal (DE)

(73) Assignee: Merck Patent GmbH, Darmstadt (DE)

( * ) Notice: Subject to any disclaimer, the term of this patent is extended or adjusted under 35 U.S.C. 154(b) by 100 days.

(21) Appl. No.: 11/443,278

(22) Filed: May 31, 2006

(65) Prior Publication Data

US 2006/0217568 A1 Sep. 28, 2006

Related U.S. Application Data

(63) Continuation of application No. 10/478,969, filed as application No. PCT/EP02/04917 on May 4, 2002, now Pat. No. 7,084,290.

(30) Foreign Application Priority Data

Jun. 1, 2001 (DE) .............................. 101 26 929
Jul. 26, 2001 (DE) .............................. 101 36 121

(51) Int. Cl.
  *C07C 303/00* (2006.01)
(52) U.S. Cl. ................. 558/54; 502/162; 429/306; 429/199; 429/200; 429/188; 429/205; 548/125; 558/44; 558/53
(58) Field of Classification Search ............. 558/54; 502/162; 429/306; 548/125
  See application file for complete search history.

(56) References Cited

U.S. PATENT DOCUMENTS

| 4,954,493 A | * | 9/1990 | Alpegiani et al. | ........... 514/195 |
| 4,962,101 A | * | 10/1990 | DiNinno et al. | ................ 514/80 |
| 5,032,587 A | * | 7/1991 | DiNinno et al. | ........ 514/210.14 |
| 5,086,374 A | | 2/1992 | MacFarlane | |

FOREIGN PATENT DOCUMENTS

| EP | 153229 | * | 8/1985 |
| JP | 04013727 | * | 1/1992 |
| JP | 04233210 | A | 12/1992 |
| JP | 06166688 | * | 6/1994 |
| WO | WO 9014676 | A | 11/1990 |
| WO | WO 0115258 | A | 3/2001 |

OTHER PUBLICATIONS

Kobayashi et al., Ring-opening polymerization and deoxothiolphostones: synthesis of poly(phosphine sulfides), Macromolecules (1986), 19(2), 462-466}.*

Jurkiewicz et al., Spin dynamics and spin counting in the 13C CP/MAS analysis of Argonne Premium coals, Fuel (1994), 73(6), 828-835.*

Visentin et al., D3-Thiazolines, D4-thiazolines and thiazoles from penem antibiotics, Heterocycles (1992), 33(2), 859-891.*

T. Gramstad, et al : "Perfluoroalkyl derivatives of sulphur. Part IV. Perfluoraalkanesulphonic acids" Journal of the Chemical Society, Nr. 1, 1956, Seiten 173-180.

T.M. Su, et al : "The solvolysis of highly unreactive substrates using the trifluoromethanesulphonate leaving group" Journal of the American Chemical Society, Bd. 91, Nr. 19, Sep. 10, 1969, Seiten 5386-5388.

D.C.R. Hockless, et al: "1-Methyl-phenylphosphirinium triflate: synthesis, structyre and reactivity" Journal of the Chemical Society, Chemical Communications, Nr. 2, Jan. 21, 1995. Seiten 257-258.

D. Yang, et al: "Design of efficient ketone catalysts for epoxidation by using the field effect" Journal of Organic Shemistry, Bd. 63, Nr. 24, Oct. 29, 1998, Seiten 8952-8956.

J.F. King, et al : "Betylates. 3. Preparative nucleophilic substitution by way of '2!-, '3!-, and '4!betylates. Stoichiometric phase transfer and substrate-reagent ion-pair (SRIP) reactions of beylates" Journal of the American Chemical Society, Bd. 104, Nr. 25, Dec. 15, 1982, Seiten 7102-7122.

S.E. Denmark, et al "Catalytic epoxidation of alkenes with oxone" Journal of Organic Chemistry, Bd. 60, Nr. 5, Mar. 10, 1995, Seiten 1391-1407.

U. Chiacchio, et al: "A general synthetic approach to 5-alkyl-2(5H) furanones via 1, 3-dipolar cycloaddition" Tetrahedron, Bd. 54, Nr. 21, May 21, 1998 Seiten 5695-5708.

S.E. Denmark, et al: Dioxiranes are the active agents in ketone-catalyzed epoxidations with oxone: Journal of Organic Chemistry, Bd. 62, Nr. 26, Dec. 26, 1997, Seiten8964-8965.

L. Ernst, et al: Darstellung und Kristallstrukturen einiger mit N, N'-Dimethyllhamstoff verbruckter Diphosphorverbindungen; NMR-Utersuchung einer gama 4P+gamma4P+-Diphosphor-verbindung Chemische Berichte, Bd. 123, Nr. 1, Jan. 1990, Seiten 35-43.

D.R.Macfarlane, et al: Pyrrolidinium imides" a new family of molten slats and conductive plastic crytal phases" Journal of Physical Chemistry B, Bd. 103, Nr. 20, May 20, 1999, Seiten 4164-4170.

Patent Abstracts of Japan vol. 16, No. 582 (E-1300), Dec. 22, 1992.

* cited by examiner

*Primary Examiner*—Sikarl A. Witherspoon
*Assistant Examiner*—Chukwuma O Nwaonicha
(74) *Attorney, Agent, or Firm*—Millen, White, Zelano, Branigan, P.C.

(57) ABSTRACT

The invention relates to a method for producing perfluoroalkanesulfonic acid esters and for further transforming the same into the salts thereof. The invention also relates to the use of the produced compounds in electrolytes, batteries, capacitors, supercapacitors, and galvanic cells.

10 Claims, No Drawings

PROCESS FOR THE PREPARATION OF COMPOUNDS CONTAINING PERFLUOROALKANESULFONIC ACID GROUPS

This application is a CON of 10/478,969 Nov. 28, 2003 U.S. Pat. No. 7,084,290 which is a 371 of PCT/EP02/C 4917 May 4, 2002.

The present invention relates to a process for the preparation of compounds containing perfluoroalkanesulfonic acid groups, and to the use of these compounds in batteries, capacitors, supercapacitors and electrochemical cells.

The spread of portable electronic equipment, such as, for example, laptop and palmtop computers, mobile telephones or video cameras, and thus also the demand for lightweight and high-performance batteries, has increased dramatically worldwide in recent years.

In view of this suddenly increased demand for batteries and the associated ecological problems, the development of rechargeable batteries with a long service life is of constantly increasing importance.

Lithium ion batteries and double layer capacitors with very high capacities (so-called super- or ultracapacitors) represent the current state of the art. In both systems, hydrolysis-sensitive and thermally unstable substances in the form of $LiPF_6$ or $N(C_2H_5)_4BF_4$ are currently used as conductive salt. In contact with moist air or with residual water from the solvents, HF can form rapidly. Besides the toxic properties, HF has a very adverse effect on the cycle behaviour and thus on the performance of the electrochemical cells.

Alternatives which have been presented are imides, such as bis(trifluoromethylsulfonyl)imide or bis(pentafluoroethylsulfonyl)imide, or methanides, such as tris(trifluoromethylsulfonyl)methanide and derivatives thereof.

However, quaternary ammonium and phosphonium salts having perfluoroalkanesulfonate anions have also been developed as conductive salts for electrochemical cells. However, the synthesis of these salts is relatively complex, since an intermediate, methyl trifluoromethanesulfonate (methyl triflate), is difficult to prepare.

Methyl triflate is a strong methylating reagent. It is used in preparative chemistry for introduction of methyl groups, for example in the methylation of heterocyclic compounds (Yu, Teylor, Tetrahedron Letter, 1999 (36), 6661-6664) or the methylation of organosulfur compounds (Tsuge, Hatta, Chem. Letter, 1997 (9), 945-946). Methyl triflate is significantly more reactive than methyl iodide, dimethyl sulfate and methyl toluenesulfonate, the methylating reagents usually used in the synthesis of quaternary ammonium and phosphonium salts.

There are various synthetic routes to methyl triflate (Gramstad, J. Chem. Soc., 1956, 173-180 or Beard, J. Org. Chem., 1973 (21), 3673-3677). None of the synthetic routes described is suitable for scale-up since they either use very toxic starting materials, such as, for example, dimethyl sulfate, the yields are very low, the reaction product has to be purified, or hazardous by-products or waste products are formed, such as, for example, sulfuric acid contaminated with dimethyl sulfate.

The object of the invention was therefore to provide a simple process for the synthesis of alkyl perfluoroalkanesulfonates and conductive salts which can be prepared therefrom.

The object is achieved by a process for the preparation of compounds containing perfluoroalkanesulfonic acid groups using a process step in which perfluoroalkanesulfonic anhydride is reacted with dialkyl carbonate in the presence of perfluoroalkanesulfonic acid to give an alkyl perfluoroalkanesulfonate, the reaction being carried out under an anhydrous atmosphere, for example:

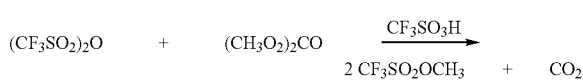

Surprisingly, it has been found that the reaction of perfluoroalkanesulfonic anhydride takes place virtually quantitatively to give the alkyl perfluoroalkanesulfonate. Only catalytic amounts of perfluoroalkanesulfonic acid are necessary; usually only 0.01-0.1 mol of perfluoroalkanesulfonic acid is necessary per mole of perfluoroalkanesulfonic anhydride.

The process according to the invention gives alkyl perfluoroalkanesulfonates which can be used as alkylating reagents. They can be used for the alkylation of heterocyclic compounds or organophosphorus and organosulfur compounds or for the preparation of N-methylamino acid with low racemate formation.

In addition, the compounds containing perfluoroalkanesulfonic acid groups obtained in accordance with the invention can also be employed in electrochemical cells, primary batteries, secondary batteries, capacitors and/or supercapacitors, for example as solvents.

Furthermore, the esters obtained can be reacted further to give perfluoroalkanesulfonic acid salts. It is advantageously not absolutely necessary for the ester initially obtained in accordance with the invention to be isolated, since unreacted dialkyl carbonates may be present as solvents in the subsequent reaction with $XR^1R^2R^3$, where
X is P or N, and
$R^1$, $R^2$ and $R^3$ are identical or different, are optionally bonded directly to one another via a single or double bond and are each, individually or together,
hydrogen,
an alkyl group having from 1 to 16 carbon atoms, which may be partially substituted by further groups, preferably F, Cl, $N(C_nF_{(2n+1-x)}H_x)_2$, $O(C_nF_{(2n+1-x)}H_x)$, $SO_2(C_nF_{(2n+1-x)}H_x)$, $C_nF_{(2n+1-x)}H_x$, where $1 \leq n \leq 6$ and $0 \leq x \leq 2n+1$, an optionally substituted aryl group or an optionally substituted heterocyclic group,
an alkylaryl group whose alkylene group has from 1 to 16 carbon atoms and which may be partially substituted by further groups, preferably F, Cl, Br, $NO_2$, CN, alkyl, aryl or a heterocyclic group,
an aryl group, which may be partially substituted by further groups, preferably F, Cl, Br, $NO_2$, CN, alkyl, aryl or a heterocyclic group, or
a heterocyclic group, which may be partially substituted by further groups, preferably F, Cl, Br, $NO_2$, CN, alkyl, aryl or a heterocyclic group,
where one, two or three $CH_2$ groups of an alkyl or alkylene group may be replaced by identical or different heteroatoms, preferably O, NH or N(alkyl) having from 1 to 6 carbon atoms, and
where $R^1$, $R^2$ and $R^3$ cannot simultaneously be perfluorinated or perchlorinated, to give the corresponding perfluoroalkanesulfonic acid salts. After the reaction, the perfluoroalkanesulfonic acid salt precipitates out. The unreacted ester merely has to be distilled off, while the remaining perfluoroalkanesulfonic acid is neutralised using $XR^1R^2R^3$ or can be used for further reactions.

In a preferred variant of the process according to the invention, the subsequent reaction with the ester is carried out using a compound $XR^1R^2R^3$ which is selected from the group consisting of

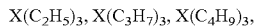

$X(C_2H_5)_3, X(C_3H_7)_3, X(C_4H_9)_3,$

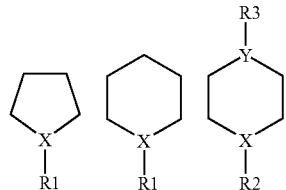

where
X and Y are P or N, and
$R^1, R^2$
and $R^3$ are, if desired, identical or different and are each, individually or together,
hydrogen,
an alkyl group having from 1 to 16 carbon atoms,
an alkylaryl group whose alkylene group has from 1 to 16 carbon atoms,
an aryl group or
a heterocyclic group,
where one, two or three $CH_2$ groups in the ring and/or the alkyl groups may be replaced by identical or different heteroatoms, preferably O, NH or N(alkyl) having from 1 to 6 carbon atoms, and
where the ring and/or the alkyl group may be partially substituted by further groups, preferably by F, Cl, $N(C_nF_{(2n+1-x)}H_x)_2$, $O(C_nF_{(2n+1-x)}H_x)$, $SO_2(C_nF_{(2n+1-x)}H_x)$, $C_nF_{(2n+1-x)}H_x$, where $1 \leq n \leq 6$ and $0 \leq x \leq 2n+1$, alkylaryl, aryl and/or a heterocyclic group, and
where the alkylaryl group, the aryl group and/or the heterocyclic group may be partially substituted by further groups, preferably F, Cl, Br, $NO_2$, CN, alkyl, aryl or a heterocyclic group.

This invention likewise relates to perfluoroalkanesulfonic acid salts of the

$M^{n+}[OSO_2CF_3]_n^-,$ type, in which $M^{n+}$ (n=1 or 2) is selected from the following group:

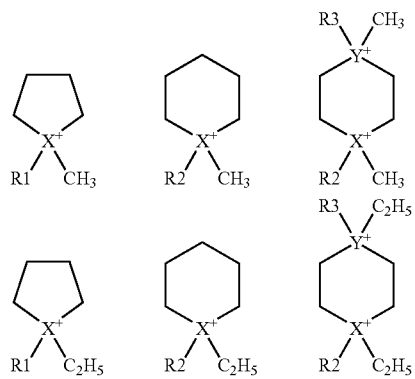

-continued

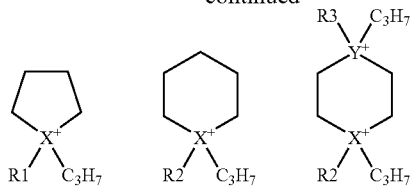

where
X and Y are P or N, and
$R^1, R^2$
and $R^3$ are, if desired, identical or different and are each, individually or together,
hydrogen,
an alkyl group having from 1 to 16 carbon atoms,
an alkylaryl group whose alkylene group has from 1 to 16 carbon atoms,
an aryl group or
a heterocyclic group,
where one, two or three $CH_2$ groups in the ring and/or the alkyl groups may be replaced by identical or different heteroatoms, preferably O, NH or N(alkyl) having from 1 to 6 carbon atoms, and
where the ring and/or the alkyl group may be partially substituted by further groups, preferably by F, Cl, $N(C_nF_{(2n+1-x)}H_x)_2$, $O(C_nF_{(2n+1-x)}H_x)$, $SO_2(C_nF_{(2n+1-x)}H_x)$, $C_nF_{(2n+1-x)}H_x$, where $1 \leq n \leq 6$ and $0 \leq x \leq 2n+1$, alkylaryl, aryl and/or a heterocyclic group, and
where the alkylaryl group, the aryl group and/or the heterocyclic group may be partially substituted by further groups, preferably F, Cl, Br, $NO_2$, CN, alkyl, aryl or a heterocyclic group.

These perfluoroalkanesulfonic acid salts can be prepared, for example, by the process according to the invention and are used in a variety of ways. Besides their use as conductive salts, for example in electrolytes, they can also be employed as solvents, in particular as ionic liquids. In addition, it is also possible to use the salts according to the invention in chemical catalysis, in particular as phase-transfer catalyst. Phase-transfer catalysis is a synthetic method which is used for a multiplicity of organic reactions and which frequently results in high yields under comparatively mild reaction conditions. In most phase-transfer-catalysed reactions, an anion is transported from an aqueous or solid phase or an interface by means of the phase-transfer catalyst into an organic phase in which it is reacted with increased reactivity. The perfluoroalkanesulfonic acid salts according to the invention are therefore suitable, inter alia, for use as ionic liquids or in phase-transfer catalysis. Their use in this respect causes no difficulties at all to the person skilled in the art.

In a further particularly preferred variant of the process according to the invention, perfluoroalkanesulfonic acid salts can be prepared by reacting an ester obtained in accordance with the invention with a compound selected from the following group:

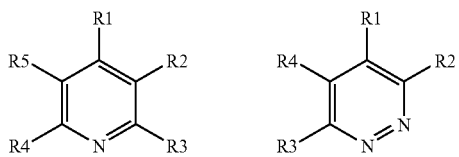

-continued

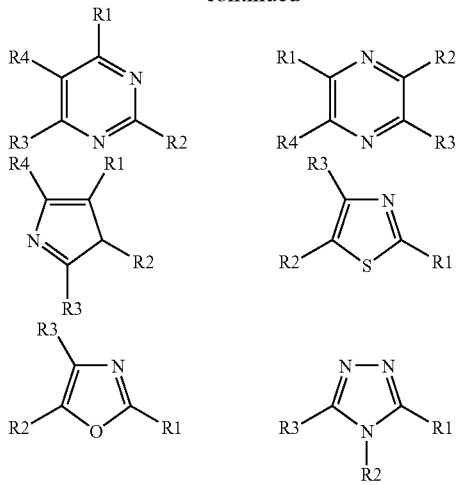

where
R¹ to R⁵ are identical or different, are optionally bonded directly to one another via a single or double bond and are each, individually or together, hydrogen, a halogen, preferably fluorine, with the proviso that no N-halogen bond is present, an alkyl group having from 1 to 8 carbon atoms, which may be partially substituted by further groups, preferably F, Cl, $N(C_nF_{(2n+1-x)}H_x)_2$, $O(C_nF_{(2n+1-x)}H_x)$, $SO_2(C_nF_{(2n+1-x)}H_x)$, $C_nF_{(2n+1-x)}H_x$, where $1 \leq n \leq 6$ and $0 \leq x \leq 2n+1$, an aryl group, an alkylaryl group, a heterocyclic group, an alkylheterocyclic group.

All compounds containing perfluoroalkanesulfonic acid groups prepared in accordance with the invention, i.e. perfluoroalkanesulfonic acid esters and in particular their salts, can be employed in electrolytes, electrochemical cells, primary and secondary batteries, capacitors, supercapacitors or ultracapacitors, for example as solvents or conductive salts. The salts can be employed as conductive salts here either in pure form or in the form of their mixtures. It is also possible to use the salts as conductive salt together with further salts known to the person skilled in the art.

The compounds containing perfluoroalkanesulfonic acid groups prepared in accordance with the invention, in particular the salts, can be used in liquid, gel-like, polymeric or solid electrolytes. To this end, mixtures comprising the conductive salts and suitable polymers and/or suitable solvents can be employed. For the purposes of the present invention, a mixture includes pure mixtures of the components, mixtures in which the salt(s) is (are) included in a polymer or gel, and mixtures in which chemical and/or physical bonds exist between the salt(s) and a polymer or gel. In the case of a gel-like electrolyte, the mixture preferably comprises a suitable solvent in addition to the salt(s) and the polymer.

The solvents employed for liquid or gel-like electrolytes are particularly preferably aprotic solvents or mixtures thereof which are suitable for use in a primary or secondary battery, a capacitor, a supercapacitor or an electrochemical cell, for example carbonates, esters, ethers, sulfolanes or nitrites, such as, for example, dimethyl carbonate, diethyl carbonate, butylene carbonate, propylene carbonate, ethylene carbonate, ethyl methyl carbonate, methyl propyl carbonate, 1,2-dimethoxyethane, 1,2-diethoxyethane, methyl acetate, γ-butyrolactone, ethyl acetate, methyl propionate, ethyl propionate, methyl butyrate, ethyl butyrate, dimethyl sulfoxide, dioxolane, sulfolane, acetonitrile, acrylonitrile, tetrahydrofuran, 2-methyltetrahydrofuran or mixtures thereof.

The polymers employed for polymeric or gel-like electrolytes are preferably homopolymers or copolymers of acrylonitrile, vinylidene difluoride, methyl (meth)acrylate, tetrahydrofuran, ethylene oxide, siloxane, phosphazene or a mixture of at least two of the above-mentioned homopolymers and/or copolymers, where it is being possible for the polymers to be at least partially crosslinked.

The electrolytes obtained in this way are suitable for use in primary batteries, secondary batteries, capacitors, supercapacitors or ultra-capacitors and electrochemical cells and are likewise a subject-matter of the present invention.

The invention also relates to primary batteries, secondary batteries, capacitors, supercapacitors and electrochemical cells which contain at least one perfluoroalkanesulfonic acid salt prepared in accordance with the invention and optionally further salts and/or additives. These further salts and additives are known to the person skilled in the art, for example from Doron Aurbach, Nonaqueous Electrochemistry, Marc Dekker Inc., New York 1999; D. Linden, Handbook of Batteries, Second Edition, McGraw-Hill Inc., New York 1995 and G. Mamantov and A. I. Popov, Chemistry of Nonaqueous Solutions, Current Progress, VCH Verlagsgemeinschaft, Weinheim 1994.

The complete disclosure content of all applications, patents and publications mentioned above and below, and the corresponding applications DE 101 26 929.3 and DE 101 36 121.1, submitted on 1 Jun. 2001 and on 26 Jul. 2001 respectively, are incorporated into this application by way of reference.

The examples of the subject-matter according to the invention which are described below serve merely for explanation and do not restrict the present invention in any way. In addition, the invention described can be carried out in the entire range claimed.

All NMR spectra were measured on a Bruker WP 80 SY spectrometer.

EXAMPLES

Example 1

Preparation of methyl trifluoromethanesulfonate (methyl triflate)

646 g (2.29 mol) of trifluoromethanesulfonic anhydride and 36 g (0.24 mol) of trifluoromethanesulfonic acid are initially introduced into a 1 l round-necked flask. 206 g (2.29 mol) of dimethyl carbonate are added at room temperature with constant stirring and reflux cooling. The solution warms to 50-60° C. within 10 minutes and is subsequently stirred at this temperature for a further 1 hour. The solution is subsequently warmed to 100-110° C. using an oil bath and stirred for a further 2 hours. After distillation, 733 g of methyl trifluoromethanesulfonate having a purity of greater than 99% are isolated (boiling range: 98-99° C., yield: 97.7%).

¹⁹F- and ¹H-NMR are identical with the literature data (Paquette, Encyclopedia of Reagents for Organic Synthesis, 1995, 3617-3622).

731 g (2.59 mol) of trifluoromethanesulfonic anhydride and 232 g (2.58 mol) of dimethyl carbonate are added to the residue, and the process described above is repeated. 837 g of methyl trifluoromethanesulfonate having a purity of greater than 99% are isolated (yield: 99.1%).

The process can be repeated a number of times.

Example 2

Preparation of methyl pentafluoroethanesulfonate 5.74 g (15.0 mmol) of pentafluoroethanesulfonic anhydride and 0.31 g (1.55 mmol) of pentafluoroethanesulfonic acid are initially introduced in a 10 ml round-necked flask. 1.35 g (15.0 mmol) of dimethyl carbonate are added at room temperature with constant stirring and reflux cooling. The solution is stirred for one hour at a temperature of 60° C. and subsequently for a further 3 hours at 110° C. After distillation, 5.41 g of methyl pentafluoroethanesulfonate are isolated (boiling range: 114-115° C., yield: 84.1%).

$^{19}$F-NMR, ppm: (solvent: CDCl$_3$; standard: CCl$_3$F): −80.44 s (CF$_3$); −115.34 s (CF$_2$)

$^{1}$H-NMR, ppm: (solvent: CDCl$_3$; standard: TMS): 4.23 s (CH$_3$)

Example 3

Preparation of N-methyl-N-triethylammonium trifluoromethanesulfonate

A solution of 8.35 g (82.7 mmol) of triethylamine in 150 cm$^3$ of dry hexane is initially introduced at room temperature. 13.56 g (82.7 mmol) of methyl triflate, prepared as in Example 1, are added at room temperature over the course of 10 minutes with constant stirring. The solution warms and is stirred for a further half an hour. During this, the solution is returned to room temperature. A white precipitate is filtered off and washed with hexane. The hexane filtrate can be used for a further reaction. After drying under reduced pressure at 60° C., 21.81 g of a white microcrystalline material are isolated (yield: 99.5%).

$^{19}$F-NMR, ppm: (solvent: acetonitrile-D$_3$; standard: CCl$_3$F): −78.04 s (CF$_3$SO$_3^-$)

$^{1}$H-NMR, ppm: (solvent: acetonitrile-D$_3$; standard: TMS): 1.25 tm (3CH$_3$); 2.86 s (CH$_3$); 3.26 q (3CH$_2$); J$^3_{H,H}$=7.3 Hz $^{1}$H-NMR data correspond to the literature data (R. Weiβ, K.-G. Wagner, M. Hertel, Chem. Ber. 117 (1984) pp. 1965-1972)

Example 4

Preparation of methyl(triethyl)phosphonium trifluoromethanesulfonate

A solution of 8.05 g (68.2 mmol) of triethylphosphine in 150 cm$^3$ of dry hexane is initially introduced at room temperature. 11.19 g (68.2 mmol) of methyl triflate, prepared as in Example 1, are added at room temperature over the course of 10 minutes with constant stirring. The solution warms and is stirred for a further half an hour. During this, the solution is returned to room temperature. A white precipitate is filtered off and washed with hexane. The hexane filtrate can be used for a further reaction. After drying under reduced pressure at 60° C., 19.02 g of a white microcrystalline material are isolated (melting point. 103-104° C., yield: 98.9%).

$^{19}$F-NMR, ppm: (solvent: acetone-D$_6$; standard: CCl$_3$F): −77.82 s (CF$_3$SO$_3^-$)

$^{1}$H-NMR, ppm (solvent: acetone-D$_6$; standard: TMS): 1.30 dt (3CH$_3$); 1.95 d (CH$_3$); 2.40 dq (3CH$_2$); J$^3_{H,H}$=7.7 Hz; J$^2_{P,H}$=13.7 Hz; J$^2_{P,H}$=13.8 Hz; J$^3_{P,H}$=18.8 Hz Elemental analysis: found: 33.72% C, 6.57% H, 11.14% S. calculated: 34.04% C, 6.43% H, 11.36% S ((C$_2$H$_5$)$_3$PCH$_3^+$ CF$_3$SO$_3^-$).

Example 5

Preparation of 1,3-dimethylimidazolium trifluoromethanesulfonate 13.70 g (83.5 mmol) of methyl triflate are added dropwise over the course of 10 minutes to 6.67 g (81.2 mmol) of 1-methylimidazole in a round-bottomed flask with stirring and ice-bath cooling. The reaction mixture warms and is stirred at 70-75° C. for one hour with reflux cooling. The excess methyl triflate is removed at 60° C. under reduced pressure. 20.00 g of a white powder are isolated.

$^{19}$F-NMR, ppm (solvent: acetonitrile-D$_3$; standard: CCl$_3$F): −78.14 s (CF$_3$SO$_3$)

$^{1}$H-NMR, ppm (solvent: acetonitrile-D$_3$; standard: TMS): 3.82 s (2CH$_3$); 7.35 d (2H); 8.53 t (1H); J$^4_{H,H}$=1.6 Hz $^{1}$H-NMR data correspond to the literature data (U. Zollner, Tetrahedron, 44, No. 24 (1988), pp. 7413-7426)

Example 6

Preparation of N,N-dimethylpyrrolidinium trifluoromethanesulfonate

A solution of 6.83 g (80.2 mmol) of N-methylpyrrolidine in 150 cm$^3$ of dry hexane is initially introduced at room temperature. 13.12 g (80.2 mmol) of methyl triflate, prepared as in Example 1, are added at room temperature over the course of 10 minutes with constant stirring, during which the solution warms. After half an hour, the solution is returned to room temperature. The white precipitate deposited is filtered off, washed with hexane and dried at 60° C. under reduced pressure. 16.61 g of a white microcrystalline material are isolated (melting point (with decomposition): 308-310° C., yield 98.3%).

$^{19}$F-NMR, ppm (solvent: acetonitrile-D$_3$; standard: CCl$_3$F): −78.00 s (CF$_3$SO$_3^-$)

$^{1}$H-NMR, ppm (solvent: acetonitrile-D$_3$; standard: TMS): 2.17 m (2H); 3.07 s (CH$_3$); 3.45 m (2H)

Elemental analysis after recrystallisation from methanol:
found: 33.66% C, 5.68% H, 5.60% N, 13.06% S.
calculated: 33.73% C, 5.66% H, 5.62% N, 12.86% S (C$_7$H$_{14}$F$_3$NO$_3$S).

Example 7

Preparation of N,N-dimethylpiperidinium trifluoromethanesulfonate

A solution of 7.76 g (78.2 mmol) of N-methylpiperidine in 150 cm$^3$ of dry hexane is initially introduced at room temperature. 12.83 g (78.2 mmol) of methyl triflate, prepared as in Example 1, are added at room temperature over the course of 10 minutes with constant stirring, during which the solution warms. After half an hour, the solution is returned to room temperature. The white precipitate deposited is filtered off, washed with hexane and dried at 80° C. under reduced pressure. 19.72 g of a white microcrystalline material are isolated (melting point after recrystallisation from methanol: 255-256° C., yield 95.8%).

$^{19}$F-NMR, ppm (solvent: acetonitrile-D$_3$; standard: CCl$_3$F): −78.06 s (CF$_3$SO$_3^-$)

$^1$H-NMR, ppm (solvent: acetonitrile-D$_3$; standard: TMS):
1.79 m (3CH$_2$); 3.02 s (2CH$_3$); 3.27 m (2CH$_2$)

Elemental analysis after recrystallisation from methanol:
found: 36.44% C, 6.07% H, 5.31% N, 12.20% S.
calculated: 36.50% C, 6.13% H, 5.32% N, 12.18% S (C$_8$H$_{16}$F$_3$NO$_3$S).

The invention claimed is:

1. A compound of the formula

in which M$^{n+}$ (n=1 or 2) is a ring of the formula

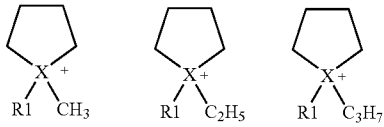

X is P or N, and
R$^1$
is
hydrogen, or
an alkyl group having from 1 to 16 carbon atoms,
where the ring is optionally partially subtituted by F, Cl, N(C$_n$F$_{(2n+1-x)}$H$_x$)$_2$, O(C$_n$F$_{(2n+1-x)}$H$_x$), SO$_2$(C$_n$F$_{(2n+1-x)}$H$_x$), C$_n$F$_{(2n+1-x)}$H$_x$, where $1 \leq n \leq 6$ and $0 \leq x \leq 2n+1$, alkylaryl, aryl and/or a heterocyclic group,
and where the alkyl group is optionally partially substituted by F, Cl, N(C$_n$F$_{(2n+1-x)}$H$_x$)$_2$, O(C$_n$F$_{(2n+1-x)}$H$_x$), SO$_2$(C$_n$F$_{(2n+1-x)}$H$_x$), C$_n$F$_{(2n+1-x)}$H$_x$, where $1 \leq n \leq 6$ and $0 \leq x \leq 2n+1$.

2. A compound of the formula M$^{n+}$

in which M$^{n+}$ (n=1 or 2) is a ring of the formula

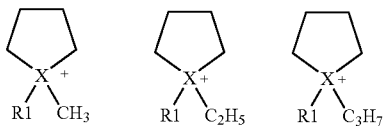

X is P or N, and
R$^1$
is
hydrogen, or
an alkyl group having from 1 to 16 carbon atoms,
where the ring and/or the alkyl group are optionally partially substituted F, Cl, N(C$_n$F$_{(2n+1-x)}$H$_x$)$_2$, O(C$_n$F$_{(2n+1-x)}$H$_x$), SO$_2$(C$_n$F$_{(2n+1-x)}$H$_x$), C$_n$F$_{(2n+1-x)}$H$_x$, where $1 \leq n \leq 6$ and $0 \leq x \leq 2n+1$.

3. Primary batteries, secondary batteries, capacitors, supercapacitors or electrochemical cells, comprising a conductive salt which is a compound of compound of the formula

in which M$^{n+}$ (n=1 or 2) is a ring of the formula

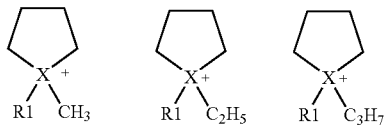

X is P or N, and
R$^1$,
is
hydrogen,
an alkyl group having from 1 to 16 carbon atoms,
an alkylaryl group whose alkylene group has from 1 to 16 carbon atoms,
an aryl group or
a heterocyclic group,
where the ring is optionally partially substituted by F, Cl, N(C$_n$F$_{(2n+1-x)}$H$_x$)$_2$, O(C$_n$F$_{(2n+1-x)}$H$_x$), SO$_2$(C$_n$F$_{(2n+1-x)}$H$_x$), C$_n$F$_{(2n+1-x)}$H$_x$, where $1 \leq n \leq 6$ and $0 \leq x \leq 2n+1$, alkylaryl, aryl and/or a heterocyclic group,
and
where the alkylaryl group and/or the heterocyclic group are optionally partially substituted, optionally in combination with further salts.

4. A liquid, gel, polymeric or solid electrolyte comprising one or more compounds according to claim 1, optionally mixed with other salts.

5. Primary batteries, secondary batteries, capacitors, supercapacitors and/or electrochemical cells comprising one or more compounds according to claim 1.

6. A solvent comprising one or more compounds according to claim 1.

7. A phase-transfer catalyst comprising one or more compounds according to claim 1.

8. Primary batteries, secondary batteries, capacitors, supercapacitors and/or electrochemical cells comprising electrolytes according to claim 4.

9. A compound according to claim 1, wherein the ring is partially substituted by F, Cl, N(C$_n$F$_{(2n+1-x)}$H$_x$)$_2$, O(C$_n$F$_{(2n+1-x)}$H$_x$), SO$_2$(C$_n$F$_{(2n+1-x)}$H$_x$), C$_n$F$_{(2n+1-x)}$H$_x$, where $1 \leq n \leq 6$ and $0 \leq x \leq 2n+1$, alkylaryl, aryl and/or a heterocyclic group.

10. A compound of the formula

in which M$^{n+}$ (n=1 or 2) is a ring of the formula

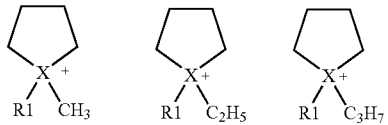

X is P or N, and
R$^1$ is hydrogen, or
unsubstituted alkyl having 1-16 C atoms.

* * * * *

UNITED STATES PATENT AND TRADEMARK OFFICE
CERTIFICATE OF CORRECTION

PATENT NO. : 7,585,994 B2
APPLICATION NO. : 11/443278
DATED : September 8, 2009
INVENTOR(S) : Ignatyev et al.

Page 1 of 1

It is certified that error appears in the above-identified patent and that said Letters Patent is hereby corrected as shown below:

Column 10, line 18 reads "where the ring is optionally partially substituted by F, Cl," should read -- where the ring and/or the alkyl group are optionally partially substituted by F, Cl, --.

Column 10, line 24 reads "where the alkylaryl group and/or the heterocyclic group are" should read -- where the alkylaryl group, the aryl group and/or the heterocyclic group are --.

Signed and Sealed this

Third Day of November, 2009

David J. Kappos
*Director of the United States Patent and Trademark Office*

UNITED STATES PATENT AND TRADEMARK OFFICE
CERTIFICATE OF CORRECTION

PATENT NO. : 7,585,994 B2 Page 1 of 1
APPLICATION NO. : 11/443278
DATED : September 8, 2009
INVENTOR(S) : Ignatyev et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 158 days.

Signed and Sealed this

Fourteenth Day of September, 2010

David J. Kappos
*Director of the United States Patent and Trademark Office*